United States Patent [19]  [11] 4,139,366
Howe  [45] Feb. 13, 1979

[54] 2-[5-ARYL-2-ISOXAZOLIN-3-YL]BENZOATES AND USE AS HERBICIDES

[75] Inventor: Robert K. Howe, Bridgeton, Mo.

[73] Assignee: Monsanto Company, St. Louis, Mo.

[21] Appl. No.: 796,111

[22] Filed: May 12, 1977

[51] Int. Cl.$^2$ .................. A01N 9/22; C07F 413/04
[52] U.S. Cl. ............................................ 71/94; 71/88;
546/275; 260/307 F
[58] Field of Search ........ 260/307 F, 295 R, 295.5 R;
71/88, 44, 76, 94

[56] References Cited
U.S. PATENT DOCUMENTS 4,032,644  6/1977  Nadelson ........................ 427/272

OTHER PUBLICATIONS

Chem. Abstracts, vol. 83, 1975, paragraph 114415h.

*Primary Examiner*—Richard Raymond
*Attorney, Agent, or Firm*—Richard H. Shear; Donald W. Peterson

[57] ABSTRACT

The invention relates to novel herbicidal 2-[5-aryl-2-isoxazolin-3-yl]benzoates and their use as agricultural chemicals.

7 Claims, No Drawings

2-[5-ARYL-2-ISOXAZOLIN-3-YL]BENZOATES AND USE AS HERBICIDES

The invention relates to novel herbicidal 2-[5-aryl-2-isoxazolin-3-yl]benzoates and their use in the preparation of 2-[5-aryl-3-isoxazolyl]benzoates. The latter compounds are effective agricultural chemicals as disclosed in Ser. No. 796,295, filed May 12, 1977.

The 2-[5-aryl-2-isoxazolin-3-yl]benzoates of the invention may be represented by the formula

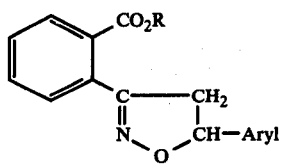

wherein R is selected from the group consisting of hydrogen, lower alkyl and agriculturally acceptable cations.

As used herein, the term "lower alkyl" or "lower alkoxy" is understood to mean those alkyl or alkoxy groups having from 1 to 5 carbon atoms, inclusive.

The term "agriculturally acceptable cations" is understood to mean those cations which are commonly used in agricultural compositions to form the salt of the free acid, including but not limited to the alkali metal, substituted amine and ammonium cations.

The term "Aryl" as used herein is understood to include pyridyl.

In accordance with the novel aspects of the present invention, the (isoxazolin-3-yl)benzoates may be prepared in accordance with the following:

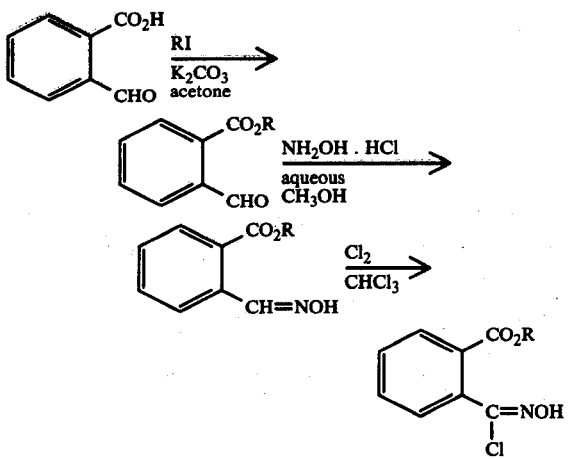

As is apparent to those skilled in the art, o-formylbenzoate may be prepared by known techniques. Addition of hydroxylamine hydrochloride in aqueous methanol results in 2-(hydroxyiminomethyl)benzoates which can be converted to the appropriate ester of benzohydroxamoyl chloride by the addition of chlorine in chloroform. Reaction of the appropriate esters of benzohydroxamoyl chloride with an olefinic benzene results in the (isoxazolin-3-yl)benzoates of the invention.

In accordance with the above procedure, and by way of example thereof, the following examples are presented.

EXAMPLE 1

Preparation of o-Methoxycarbonylbenzohydroxamoyl Chloride

Methyl o-formylbenzoate was prepared in 81% yield from 2-carboxybenzaldehyde by the procedure of Brown and Sargent, Journal Chemical Society, P 1818 (1969). A solution of 1.64 g (0.010 mol) of methyl o-formylbenzoate and 1.05 g (.015 mol) of hydroxylamine hydrochloride in 95 ml of 30% aqueous methanol was stirred at 23° C. for 50 minutes and then was cooled in ice. Scratching induced crystallization of 0.70 g of white solid (mp 73°–74.5° C.) which was methyl 2-(hydroxyiminomethyl)benzoate. Chlorine gas was slowly bubbled into a solution of 7.87 g (.0439 mol) of methyl 2-(hydroxyiminomethyl)benzoate in 250 ml of $CHCl_3$ stirred at 0° C. (ice-methanol bath). A blue color formed, and the clear solution became cloudy. Within a few minutes, the blue reaction mixture turned green. After about 20 minutes, excess chlorine gas began to come through the solution, so chlorine addition was stopped and the solution was stirred in an ice bath for 1 hour until the green color had nearly all faded. Nitrogen gas was bubbled through the solution as it was allowed to warm to 20° C. during 30 minutes. The solution was concentrated under aspirator vacuum at 30°–40° C. The residue was triturated with 50 ml of ether, and the supernatant was decanted from a little insoluble gum and was concentrated to 7.21 g of viscous oil. This compound was identified as o-methoxycarbonylbenzohydroxamoyl chloride, ir 2.95, 5.80 μ.

EXAMPLE 2

Preparation of Methyl 2-[5-[3-(Trifluoromethyl)Phenyl]2-Isoxazolin-3-yl]Benzoate To a solution of 12.3 g (.0714 mol) of m-trifluoromethylstyrene and 15.6 g (.073 mol) of o-(methoxycarbonyl)benzohydroxamoyl chloride in 200 ml of ether stirred at 0°–5° C. was added dropwise a solution of 9.43 g (.073 mol) of ethyldiisopropylamine in 35 ml of ether during 45 minutes. The mixture was stirred at 0°–5° C. for another 2 hours and then at 20° C. for 3 hours. Ether, 50 ml, was added, and the mixture was extracted three times with 200-ml portions of water. The ether layer was dried ($CaSO_4$) and concentrated under vacuum to 90° C. at 0.5 torr to give 18.4 g of residual oil.

Chromatography of 4.0 g of the oil on 150 g of Woelm silica gel with 2% ether in benzene gave, after an initial 540 ml of eluate, 3.38 g of pure product in the next 380 ml of eluate. The product, an oil, had $n_D^{25}$ 1.5412; ir ($CHCl_3$) 5.80 μ.

Anal. Calc'd. for $C_{18}H_{14}F_3NO_3$: C, 61.89; H, 4.04. Found: C, 62.07; H, 4.07.

EXAMPLE 3

Preparation of Methyl 2-[5-(1-Naphthyl)-2-Isoxazolin-3-yl]Benzoate

To a solution of 10.82 g (.0702 mol) of 1-vinylnaphthalene and 15.0 g (.0702 mol) of o-(methoxycarbonyl)-benzohydroxamoyl chloride in 200 ml of ether stirred at 0°–5° C. was added dropwise a solution of 9.07 g (.0702 mol) of ethyldiisopropylamine in 35 ml of ether during 45 minutes. The mixture was stirred for another 2 hours at 0°–5° C. and for 24 hours at 20° C. and then was washed three times with water, dried ($CaSO_4$), and concentrated under aspirator vacuum. The residue was concentrated further in a Kugelrohr apparatus at 125° C. at 0.15 torr (to remove excess 1-vinylnaphthalene) to give 15.2 g of "glass".

Chromatography of 4.77 g of the material on 150 g of Woelm silica gel with 5% ether in benzene gave nil in the first 400 ml of eluate, and then 4.53 g of pure product as a "glass" in the next 280 ml of eluate; ir ($CHCl_3$) 5.80 μ.

Anal. Calc'd. for $C_{21}H_{17}NO_3$: C, 76.12; H, 5.17. Found: C, 75.87; H, 5.18.

EXAMPLE 4

Preparation of Methyl 2-[5-(2-Pyridyl)-2-Isoxazolin-3-yl]Benzoate

A solution of 7.38 g (.0702 mol) of 2-vinylpyridine and 9.07 g (.0702 mol) of ethyldiisopropylamine in 60 ml of ether was added dropwise during 20 minutes to a solution of 15.0 g (.0702 mol) of o-(methoxycarbonyl)-benzohydroxamoyl chloride in 200 ml of ether stirred at 0°–5° C. The mixture was stirred at 0°–5° C. for another 2 hours and then at 20° C. for 24 hours and then was washed twice with aqueous $NaHCO_3$ solution and once with aqueous NaCl solution. The ether layer was dried ($CaSO_4$) and analyzed by ir, which revealed some nitrile oxide to be left. The ether solution was allowed to stand another 48 hours and then was concentrated to 90° C. at 0.15 torr to give 14.23 g of viscous oil.

A 3.23 g sample of the oil was chromatographed on 150 g of Woelm silica gel with 10% ether in benzene. After an initial 1300 ml of eluate, 2.28 g of product was eluted; ir ($CHCl_3$) 5.80 μ. A small sample was subjected to Kugelrohr distillation at 145° C. (.03 torr) for analysis.

Anal. Calc'd. for $C_{16}H_{14}N_2O_3$: C, 68.15; H, 5.00. Found: C, 67.89; H, 5.10.

Similarly, the following compounds have been prepared:

| Example | Compound |
|---|---|
| 5 | Methyl 2-[5-(4-Chlorophenyl)-2-Isoxazolin-3-yl]Benzoate. Anal. Calc'd. for $C_{17}H_{14}ClNO_3$: C, 64.67; H, 4.47. Found: C, 64.48; H, 4.50. |
| 6 | Methyl 2-[5-(4-Methoxyphenyl)-2-Isoxazolin-3-yl]Benzoate. Anal. Calc'd. for $C_{18}H_{17}NO_4$: C, 69.44; H, 5.50. Found: C, 69.37; H, 5.50. |
| 7 | Methyl 2-[5-(4-Methylphenyl)-2-Isoxazolin-3-yl]Benzoate. Anal. Calc'd.: C, 73.22; H, 5.76; N, 4.75. Found: C, 73.06; H, 5.82; N, 4.72. |
| 8 | Methyl 2-[5-(4-Pyridyl)-2-Isoxazolin-3-yl]Benzoate. Anal. Calc'd. for $C_{16}H_{14}N_2O_3$: C, 68.08; H, 5.00. Found: C, 67.80; H, 5.09. |
| 9 | Methyl 2-[5-(3,4-Methylenedioxyphenyl)-2-Isoxazolin-3-yl]Benzoate. Anal. Calc'd. for $C_{18}H_{15}NO_5$: C, 66.46; H, 4.65. Found: C, 66.46; H, 4.66. |

The compounds of the invention have been found to be effective in controlling the growth of undesired vegetation. Table I summarizes results of tests conducted to determine the pre-emergent as well as the post-emergent herbicidal activity of the compounds.

The pre-emergent test was conducted as follows:

A good grade of top soil was placed in aluminum pans and compacted to a depth of three-eighths to one-half inch from the top of the pan. On the top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

Unless noted otherwise, approximately 28 days after seeding and treating, the plants were observed and the results recorded. The herbicidal rating was obtained by means of a fixed scale based on the average percent injury of each seed lot. The ratings are defined as follows:

| % Control | Rating |
|---|---|
| 0–24 | 0 |
| 25–49 | 1 |
| 50–74 | 2 |
| 75–100 | 3 |

The post-emergent tests were conducted as follows:

The active ingredients are applied in spray form to 2 or 3-week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately 28 days later the effects ranging from partial to total inhibition are observed and recorded. The results are shown in Table I in which the post-emergent herbicidal activity index is as follows:

| % Control | Rating |
|---|---|
| 0–24 | 0 |
| 25–49 | 1 |
| 50–74 | 2 |
| 75–99 | 3 |
| 100 | 4 |

The plant species utilized in these tests are identified by letter in accordance with the following legend:

| A | Canada Thistle | G | Nutsedge |
| B | Cocklebur | H | Quackgrass |
| C | Velvet Leaf | I | Johnson Grass |
| D | Morning Glory | J | Downy Brome |
| E | Lambsquarters | K | Barnyard Grass |
| F | Smartweed | | |

The results are summarized by Table I.

Table I

| | | Pre-Emergent Plant Species | | | | | | | | | | |
|---|---|---|---|---|---|---|---|---|---|---|---|---|
| Compound | kg/h | A | B | C | D | E | F | G | H | I | J | K |
| 2 | 11.2 | 1 | 1 | 1 | 1 | 1 | 1 | 0 | 2 | 0 | 1 | 3 |
| 3 | 11.2 | 0 | 0 | 0 | 0 | 0 | 1 | 0 | 1 | 0 | 0 | 2 |
| 4 | 11.2 | 0 | 0 | 1 | 0 | 0 | 0 | 2 | 2 | 2 | 0 | 0 |
| 5 | 11.2 | 0 | 1 | 1 | 0 | 2 | 1 | 0 | 2 | 0 | 0 | 2 |
| 6 | 11.2 | 1 | 1 | 1 | 2 | 3 | 1 | 0 | 2 | 0 | 0 | 0 |
| 7 | 11.2 | 0 | 0 | 2 | 2 | 1 | 0 | 1 | 0 | 0 | 0 | 0 |
| 8 | 11.2 | 0 | 0 | 0 | 0 | 0 | 0 | 0 | 0 | 0 | 0 | 0 |
| 9 | 11.2 | 3 | 1 | 1 | 0 | 0 | 0 | 0 | 1 | 0 | 3 | 0 |

Post-Emergent Plant Species

Table I-continued

| Compound | Kg/h | A | B | C | D | E | F | G | H | I | J | K |
|---|---|---|---|---|---|---|---|---|---|---|---|---|
| 2 | 11.2 | 1 | 1 | 0 | 1 | 0 | 0 | 0 | 1 | 0 | 0 | 0 |
| 3 | 11.2 | 1 | 1 | 0 | 1 | 1 | 0 | 0 | 0 | 0 | 0 | 1 |
| 4 | 11.2 | 0 | 0 | 1 | 0 | 2 | 0 | 0 | 1 | 0 | 1 | 2 |
| 5 | 11.2 | 1 | 1 | 1 | 1 | 1 | 1 | 0 | 1 | 0 | 0 | 1 |
| 6 | 11.2 | 0 | 1 | 1 | 1 | 2 | 1 | 0 | 0 | 0 | 0 | 0 |
| 7* | 11.2 | 0 | 1 | 1 | 1 | 1 | 0 | 0 | 0 | — | 0 | 1 |
| 8 | 11.2 | 0 | 0 | 0 | 0 | 1 | 0 | 0 | 0 | 0 | 0 | 1 |
| 9 | 11.2 | 0 | 0 | 0 | 0 | 0 | 0 | 0 | 0 | 0 | 0 | 0 |

*Plants observed 14 days after treatment

In the practice of the invention, the compounds when used as a herbicide can be used alone or in combination with a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 1 to 99 parts active ingredient, about 1 to 50 parts surface-active agent and about 4 to 94 parts solvents, all parts being by weight based on the total weight of the composition.

Preferred are those compounds in which Aryl is phenyl or phenyl substituted by one or more halogen, trifluoromethyl, lower alkyl or lower alkoxy moieties. Further preferred are those in which R is lower alkyl.

The novel (isoxazolin-3-yl)benzoates of the invention may be converted to the isoxazolyl benzoates by reaction with N-bromosuccinimide or dichlorodicyanobenzoquinone. Examples of this procedure are set out in Ser. No. 796,295, filed May 12, 1977 which is hereby incorporated by reference.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

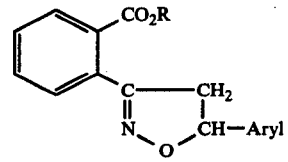

wherein R is selected from the group consisting of hydrogen, lower alkyl and agriculturally acceptable cations; and Aryl is pyridyl, naphthyl, phenyl or phenyl substituted by one or more halogen, trifluoromethyl, lower alkyl or lower alkoxy moieties.

2. A compound according to claim 1 wherein Aryl is phenyl or phenyl substituted by one or more halogen, trifluoromethyl, lower alkyl or lower alkoxy moieties.

3. A compound according to claim 1 wherein Aryl is pyridyl.

4. A compound according to claim 1 wherein R is lower alkyl.

5. A compound according to claim 1 wherein R is naphthyl.

6. A method for controlling the growth of undesired vegetation which comprises applying thereto a herbicidally effective amount of a compound having the formula

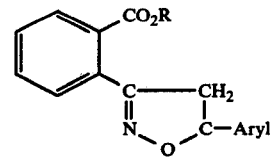

wherein R is selected from the group consisting of hydrogen, lower alkyl and agriculturally acceptable cations; and Aryl is pyridyl, naphthyl, phenyl or phenyl substituted by one or more halogen, trifluoromethyl, lower alkyl or lower alkoxy moieties.

7. A herbicidal composition which comprises from about 1 to about 99 parts by weight of a compound having the formula

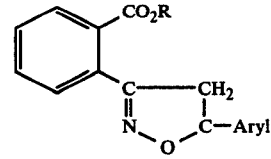

wherein R is selected from the group consisting of hydrogen, lower alkyl and agriculturally acceptable cations; and Aryl is pyridyl, naphthyl, phenyl or phenyl substituted by one or more halogen, trifluoromethyl, lower alkyl or lower alkoxy moieties; the remaining parts being composed of one or more adjuvants, carriers and/or diluents.

* * * * *